United States Patent [19]
Ramin et al.

[11] Patent Number: 5,910,313
[45] Date of Patent: Jun. 8, 1999

[54] USE OF COLLOIDAL SILICIC ACID IN A NAIL VARNISH COMPOSITION

[75] Inventors: Roland Ramin, Itteville; Jean-Claude Garson, Suresnes, both of France

[73] Assignee: L'Oreal, Paris, France

[21] Appl. No.: 08/895,860

[22] Filed: Jul. 17, 1997

[30]     Foreign Application Priority Data

Jul. 18, 1996 [FR] France ..................... 96 09010

[51] Int. Cl.$^6$ ............... A61K 6/00; A61K 7/00; A61K 7/04
[52] U.S. Cl. .............. 424/401; 424/61
[58] Field of Search ...................... 424/61, 401

[56]     References Cited

U.S. PATENT DOCUMENTS

| | | | |
|---|---|---|---|
| 5,071,639 | 12/1991 | Soyama et al. | 424/61 |
| 5,275,807 | 1/1994 | Pappas et al. | 424/61 |
| 5,725,882 | 3/1998 | Kumar et al. | 424/486 |

FOREIGN PATENT DOCUMENTS

| | | |
|---|---|---|
| 0 063 467 | 10/1982 | European Pat. Off. . |
| 0 453 628 | 10/1991 | European Pat. Off. . |
| 0 504 754 | 3/1992 | European Pat. Off. . |
| 0 745 372 | 12/1996 | European Pat. Off. . |
| 2 578 741 | 9/1986 | France . |
| 884626 | 12/1961 | United Kingdom . |

OTHER PUBLICATIONS

Chemical Abstracts, vol. 123, No. 10, Sep. 4, 1995.
Patent Abstracts of Japan, vol. 96, No. 8, Apr. 9, 1996.
Chemical Abstracts, vol. 121, No. 26, Dec. 26, 1994.
English Derwent Abstract of EP 0 745 372 (1997).
English Derwent Abstract of EP 0 504 754 (1997).
English Derwent Abstract of FR 2 578 741 (1997).
English Derwent Abstract of EP 0 453 628 (1997).

*Primary Examiner*—Thurman K. Page
*Assistant Examiner*—Sharon Howard
*Attorney, Agent, or Firm*—Finnegan, Henderson, Farabow, Garrett & Dunner, L.L.P.

[57]     ABSTRACT

The use of colloidal silicic acid as strengthening agent in a composition comprising at least one film-forming material and at least one solvent, particularly an organic, aqueous or oily solvent.

23 Claims, No Drawings

USE OF COLLOIDAL SILICIC ACID IN A NAIL VARNISH COMPOSITION

The present invention relates to the use of colloidal silicic acid in a nail varnish composition in a solvent medium such as an organic, aqueous or oily solvent medium.

Compositions to be applied, for example on the nail, of nail varnish or nail care base type in solvent medium, conventionally comprising at least one film-forming polymer, optionally a plasticizing agent, pigments, rheological agents and solvents, are known.

Such a composition can thus make it possible to beautify the nail. However, the compositions known to date exhibit the fault of rapidly wearing away, which obliges the user to repeat, at very frequent time intervals, the application of a fresh layer of varnish after removal of the damaged layer.

This fault of nail care bases and of nail varnishes has led the inventors to search for agents which, incorporated in a varnish or care base composition for the nails, would confer, on the films obtained from the latter, a greater surface hardness and, consequently, would increase the films' resistance to rubbing and/or to impacts.

The inventors have found, surprisingly, that colloidal silicic acid could be used satisfactorily to improve the surface hardness of the films obtained using conventional varnishes and care bases for the nail.

The subject of the present invention is consequently the use of colloidal silicic acid as strengthening agent in a varnish or nail care base composition comprising at least one film-forming material and at least one solvent, particularly an organic and/or aqueous and/or oily solvent.

"Strengthening agent" is understood to mean, in the present description, an agent capable of improving the surface hardness of a film of a varnish or care base composition deposited on a substrate, in particular a keratinous substrate, such as a nail.

The use of a composition according to the invention on the nails thus makes it possible to obtain a varnish or base film which exhibits a better surface hardness and consequently a greater lifetime (better resistance to attacks, such as impacts, rubbing, scratches or pressure).

The composition according to the invention thus comprises at least one film-forming material. When the care base or the varnish according to the invention is a composition in organic solvent medium, the film-forming material can be chosen in particular from alkyd, acrylic and/or vinyl resins, polyurethanes and polyesters, cellulose and cellulose derivatives, such as nitrocellulose, and the resins resulting from the condensation of formaldehyde with an arylsulfonamide, and their mixtures.

In this case, the film-forming material is generally in solution, for example at 5–25% by weight, in an organic solvent, such as an aromatic hydrocarbon, for example toluene or xylene, an aliphatic hydrocarbon, for example n-heptane, an ester, for example ethyl acetate or butyl acetate, a ketone, for example acetone or methyl ethyl ketone, an alcohol, for example ethanol, isopropanol or butanol, and their mixtures..

When the care base or the nail varnish according to the invention is a composition in aqueous medium, the composition can comprise the polymer in the form of dispersed film-forming polymer particles.

Mention may be made, among the film-forming polymers capable of being used, of polyurethanes, for example anionic polyurethanes, polyesters-polyurethanes, polyethers-polyurethanes, radical polymers, in particular of acrylic, acrylic-styrene and/or vinyl type, polyesters or alkyd resins, alone or as a mixture.

The dispersion can also comprise an associative polymer of polyurethane type or a natural gum, such as xanthan gum.

The composition preferably exhibits a dry matter content of 25–45% by weight.

The composition can also comprise a plasticizing agent and optionally Theological agents. Representative plasticizing agents include citrates, phthalates, esters and/or camphor, generally used in an amount of 5–30% by weight with respect to the weight of the composition. Representative rheological agents, of organophilic bentonites, cellulose derivatives, crosslinked polyacrylic acid derivatives, guar gum or locust bean gum, as well as xanthan gums.

The colloidal silicic acid capable of being used in the composition according to the invention is preferably a pyrogenic or surface-treated silica which can be provided in the form of a hydrophilic pyrogenic silica, a hydrophobic pyrogenic silica or a silica surface-treated by an organic treatment.

The pyrogenic silicas can be obtained by high-temperature hydrolysis of a volatile silicon compound in an oxyhydrogen flame. This results in the production of a finely divided silica. It is possible, by reaction, to chemically modify the surface of the said silica by reduction of the number of silanol groups, in order to obtain a hydrophobic silica.

The colloidal silicic acid preferably exhibits a particle size which can be nanometric to micrometric, for example in the order of 10–200 nm.

The colloidal silicic acid according to the invention can be, inter alia, chosen from the compounds sold by Degussa under the trade names Aerosil MOX80 or Aerosil COK84, which are special silicas, Aerosil R972, which is a hydrophobic silica, or alternatively Aerosil OK412, which is a surface-treated silica, or under the trade name Aerosil 200, which is a hydrophilic silica.

The composition according to the invention can comprise colloidal silicic acid preferably in an amount of 0.05% to 5% by weight, more preferably in an amount of 0.5 to 2% by weight, with respect to the total weight of the composition.

The composition according to the invention can additionally comprise any additive known to the person skilled in the art as being capable of being incorporated in such a composition, such as spreading agents, wetting agents, dispersing agents, antifoaming agents, preservatives, UV screening agents, dyes, pigments, pearlescent agents, active principles, such as n-butylformyl, D-panthenol or phytantriol, vitamins and their derivatives, keratin and its derivatives, melanin, collagen, cystine, chitosan and its derivatives, ceramides, biotin, trace elements, glycerol, protein hydrolysates, phospholipids or moisturizing agents. The person skilled in the art will, of course, take care to choose this or these possible additional compounds, and/or their amount, so that the advantageous properties of the composition according to the invention are not, or not substantially, detrimentally affected by the envisaged addition.

The composition according to the invention can be prepared by the person skilled in the art on the basis of his overall knowledge and according to the state of the art.

The composition according to the invention can be provided in the form of a product to be applied on the nails, such as a varnish, a base or a care base.

The Vickers hardness tests show a greater hardness of the varnishes according to the invention in comparison with the varnishes which do not contain silica or in comparison with the varnishes which comprise other additives. The invention is illustrated in more detail in the following examples.

EXAMPLES

The hardness of a varnish comprising colloidal silicic acid was determined.

Principle:

A nail varnish to be tested is applied on the nail and there is a wait until the nail is dry.

A penetrometer is applied on the nail in the form of a square-based pyramid, using a load P. The average size of a diagonal of the square impression obtained with the penetrometer is then determined.

The Vickers hardness ($H_v$) is then determined, from the relationship:

$$H_V = \frac{1854.4 \times P}{d^2}$$

wherein d=average diagonal in $\mu$m, and P=load applied in g.

The Vickers hardness is measured according to ASTM Standard E384-89 using an M 400 g 2 microhardness tester from the Leco company.

EXAMPLE 1

A nail varnish is prepared which has the following composition (% by weight):

| | |
|---|---|
| nitrocellulose | 15% |
| tributyl acetylcitrate | 6% |
| tosylamide-formaldehyde resin | 10% |
| colloidal silicic acid (Aerosil 200 from Degussa) | 1% |
| solvent (ethyl acetate and butyl acetate) | q.s. for 100% |

A varnish with an appropriate texture is obtained which is applied readily on the nail. It makes it possible, after drying, to obtain a smooth and homogeneous film.

Vickers hardness: $H_v$=5.8

EXAMPLE 2: Control varnish

A nail varnish is prepared which has the following composition (% by weight):

| | |
|---|---|
| nitrocellulose | 15% |
| tributyl acetylcitrate | 6% |
| tosylamide-formaldehyde resin | 10% |
| solvent (ethyl acetate and butyl acetate) | q.s. for 100% |

Vickers hardness: $H_v$=4.8

EXAMPLE 3: Control varnish

A nail varnish is prepared which has the following composition (% by weight):

| | |
|---|---|
| nitrocellulose | 15% |
| tributyl acetylcitrate | 6% |
| tosylamide-formaldehyde resin | 10% |
| stearalkonium hectorite (CTFA name) | 1% |
| solvent (ethyl acetate and butyl acetate) | q.s. for 100% |

Vickers hardness: $H_v$=4.5

It is found that the varnishes according to the invention (Example 1) give a film with a surface hardness which is greater than the surface hardness of a film obtained from a composition which does not comprise a rheological agent (Example 2) or from a composition comprising a rheological agent of the Bentone type (Example 3).

We claim:

1. A method comprising applying a varnish or nail care composition on a substrate, wherein said composition comprises:

at least one colloidal silicic acid present in an amount effective to provide surface hardness and resistance to penetration or deformation to a film formed from applying said composition on the substrate, at least one film-forming material and at least one solvent.

2. The method of claim 1 wherein said substrate is a keratinous substrate.

3. The method of claim 2 wherein said keratinous substrate is a nail.

4. The method of claim 1 wherein said at least one solvent is organic.

5. The method of claim 1 wherein said at least one solvent is aqueous.

6. The method of claim 1 wherein said at least one solvent is oily.

7. The method of claim 2 wherein said substrate is a keratinous substrate.

8. The method of claim 7 wherein said keratinous substrate is a nail.

9. The method of claim 2 wherein said at least one solvent is organic.

10. The method of claim 2 wherein said at least one solvent is aqueous.

11. The method of claim 2 wherein said at least one solvent is oily.

12. The method of claim 1 wherein said at least one colloidal silicic acid is a surface-treated silica, a hydrophilic pyrogenic silica or a hydrophobic pyrogenic silica.

13. The method of claim 1 wherein said at least one colloidal silicic acid is present in an amount of 0.05% to 5% by weight, with respect to the total weight of the composition.

14. The method of claim 13 wherein said at least one colloidal silicic acid is present in an amount of 0.5 to 2% by weight, with respect to the total weight of the composition.

15. The method of claim 4 wherein said at least one film-forming material is an alkyd, acrylic or vinyl resin, a polyurethane or polyester, cellulose or a cellulose derivative, or a resin resulting from the condensation of formaldehyde with an arylsulfonamide.

16. The method of claim 15 wherein said cellulose derivative is nitrocellulose.

17. The method of claim 4 wherein said at least one organic solvent is toluene, xylene, ethyl acetate, butyl acetate, a ketone, a glycol ether, an ester, ethanol, isopropanol or butanol.

18. The method of claim 5 wherein said at least one film-forming material comprises dispersed film-forming polymer particles, said particles being polyurethane polyester-polyurethane, polyether-polyurethane, a radical polymer of acrylic, acrylic styrene, or acrylic vinyl, polyester or an alkyd resin.

19. The method of claim 18 wherein said composition further contains at least one dispersed associative polymer, wherein said associative polymer is polyurethane or a natural gum.

20. The method of claim 19 wherein said natural gum is xanthan gum.

21. The method of claim 1 wherein said composition comprises a dry matter content of 25 to 45% by weight.

22. The method of claim 1 wherein said composition further comprises at least one plasticizing agent, wherein said at least one plasticizing agent is a citrate, phthalate, ester or camphor, and is present in an amount of 5 to 30% by weight with respect to the weight of the composition.

23. A method for improving the surface hardness and resistance to penetration or deformation of a film formed from applying a varnish or nail composition on a substrate, said method comprising applying said varnish or nail care composition on said substrate, wherein said composition comprises:

at least one colloidal silicic acid present in an amount effective to provide surface hardness and resistance to penetration or deformation to a film formed from applying said composition on the substrate, at least one film-forming material and at least one solvent.

* * * * *

UNITED STATES PATENT AND TRADEMARK OFFICE
CERTIFICATE OF CORRECTION

PATENT NO.: 5,910,313
DATED: June 8, 1999
INVENTOR(S): Roland RAMIN et al.

It is certified that an error appears in the above-identified patent and that said Letters Patent is hereby corrected as shown below:

Claim 7, col. 4, line 17, "claim 2" should read --claim 23--.

Claim 9, col. 4, line 20, "claim 2" should read --claim 23--.

Claim 10, col. 4, line 22, "claim 2" should read --claim 23--.

Claim 11, col. 4, line 24, "claim 2" should read --claim 23--.

Claim 18, col. 4, line 49, "polyurethane" should read --polyurethane,--.

Signed and Sealed this

Sixteenth Day of November, 1999

Attest:

Q. TODD DICKINSON

*Attesting Officer*   *Acting Commissioner of Patents and Trademarks*